US008350183B2

(12) United States Patent
Vogel et al.

(10) Patent No.: US 8,350,183 B2
(45) Date of Patent: Jan. 8, 2013

(54) METHOD FOR LASER MACHINING TRANSPARENT MATERIALS

(75) Inventors: Alfred Vogel, Lubeck (DE); Norbert Linz, Lubeck (DE); Sebastian Freidank, Lubeck (DE)

(73) Assignee: Universitat Zu Lubeck, Lubeck (DE)

( * ) Notice: Subject to any disclaimer, the term of this patent is extended or adjusted under 35 U.S.C. 154(b) by 489 days.

(21) Appl. No.: 12/663,728

(22) PCT Filed: Jun. 7, 2008

(86) PCT No.: PCT/DE2008/000955
§ 371 (c)(1),
(2), (4) Date: Dec. 9, 2009

(87) PCT Pub. No.: WO2008/151616
PCT Pub. Date: Dec. 18, 2008

(65) Prior Publication Data
US 2010/0163540 A1 Jul. 1, 2010

(30) Foreign Application Priority Data
Jun. 14, 2007 (DE) .......... 10 2007 028 042

(51) Int. Cl.
*B23K 26/04* (2006.01)
*B23K 26/00* (2006.01)
*B23K 26/02* (2006.01)
(52) U.S. Cl. ......... 219/121.62; 219/121.69; 219/121.83; 219/121.85
(58) Field of Classification Search .......... None
See application file for complete search history.

(56) References Cited

U.S. PATENT DOCUMENTS

| 5,656,186 | A | * | 8/1997 | Mourou et al. | 219/121.69 |
|---|---|---|---|---|---|
| 6,333,485 | B1 | * | 12/2001 | Haight et al. | 219/121.68 |
| RE37,585 | E | * | 3/2002 | Mourou et al. | 219/121.69 |
| 6,552,301 | B2 | * | 4/2003 | Herman et al. | 219/121.71 |
| 6,587,136 | B2 | * | 7/2003 | Hayashi | 347/224 |
| 6,670,576 | B2 | * | 12/2003 | Troitski et al. | 219/121.69 |
| 6,787,733 | B2 | * | 9/2004 | Lubatschowski et al. | 219/121.67 |
| 6,884,960 | B2 | * | 4/2005 | Bourne et al. | 219/121.69 |
| 6,995,336 | B2 | * | 2/2006 | Hunt et al. | 219/121.69 |
| 7,060,933 | B2 | * | 6/2006 | Burrowes et al. | 219/121.69 |

(Continued)

FOREIGN PATENT DOCUMENTS
DE 19855623 2/2000
(Continued)

OTHER PUBLICATIONS

Krausz et al. Femtosecond Solid-State Lasers. Oct. 1992. IEEE Journal of Quantum Electronics. vol. 28. No. 10. pp. 2097-2122.*

(Continued)

*Primary Examiner* — Hoang-Quan Ho
(74) *Attorney, Agent, or Firm* — Diederiks & Whitelaw, PLC

(57) ABSTRACT

A method for machining a transparent material by the non-linear absorption of pulsed laser radiation, in the region of a laser focus, includes the following steps: a laser wavelength of between 300 and 1000 μm is selected; and laser impulses having a temporally flat beam profile are applied. The method is characterized in that the irradiation intensity is selected from an interval pre-determined for the material to be machined, in which plasma is formed without plasma luminescence. An apparatus for laser treating a transparent material includes structure to set an irradiance and inspect the treatment as being within a defined interval.

11 Claims, 3 Drawing Sheets

U.S. PATENT DOCUMENTS

| | | | |
|---|---|---|---|
| 7,560,658 B2* | 7/2009 | Hunt et al. | 219/121.61 |
| 7,649,153 B2* | 1/2010 | Haight et al. | 219/121.69 |
| 7,767,931 B1* | 8/2010 | Welle et al. | 219/121.72 |
| 2005/0064137 A1* | 3/2005 | Hunt et al. | 428/131 |
| 2005/0167410 A1* | 8/2005 | Bourne et al. | 219/121.85 |
| 2006/0175312 A1* | 8/2006 | Troitski | 219/121.85 |
| 2006/0207976 A1* | 9/2006 | Bovatsek et al. | 219/121.69 |
| 2007/0045252 A1* | 3/2007 | Kleine et al. | 219/121.69 |
| 2007/0045255 A1* | 3/2007 | Kleine et al. | 219/121.72 |
| 2008/0105663 A1* | 5/2008 | Hunt et al. | 219/121.69 |
| 2009/0045179 A1* | 2/2009 | Williams | 219/121.72 |
| 2010/0108651 A1* | 5/2010 | Stahr | 219/121.69 |

FOREIGN PATENT DOCUMENTS

| | | |
|---|---|---|
| DE | 10323422 | 4/2004 |
| WO | 2008/086772 | 7/2008 |

OTHER PUBLICATIONS

Colombelli et al., "Ultraviolet Diffraction Limited Nanosugery of Live Biological Tissues", Review of Scientific Instruments, vol. 75, No. 2, pp. 472-478, Feb. 2004.

Vogel et al., "Mechanisms of Femtosecond Laser Nanosurgery of Cells and Tissues", Applied Physics B, vol. 81, No. 8, pp. 1015-1047, 2005.

* cited by examiner

METHOD FOR LASER MACHINING TRANSPARENT MATERIALS

CROSS-REFERENCE TO RELATED APPLICATIONS

This application represents a National Stage application of PCT/DE2008/000955 entitled "Method for Laser Machining Transparent Materials" filed Jun. 7, 2008, pending.

BACKGROUND OF THE INVENTION

The invention relates to a method for laser machining transparent materials, in particular for producing precise, localised changes of material inside a transparent body.

Generating very tine effects during laser material machining requires localised deposition of very small amounts of energy. When energy is deposited by linear absorption (single-photon absorption), the desired high precision of the material machining requires a small optical penetration depth of the laser radiation as well as a sufficiently short length of the laser pulse so as to avoid heat diffusion during the duration of the laser pulse.

In transparent materials such as glass, quartz, water, body tissue without pigments, or cells, energy can be deposited in a localised fashion only through non-linear absorption, that is to say by multiple-photon processes in the form of multi-photon ionisation and avalanche ionisation that lead to the formation of a plasma (quasi-free charge carriers in the material consisting of a mixture of electrons and ions). Since the occurrence of multi-photon processes is a non-linear function of the laser light intensity, this is referred to as "non-linear absorption". And since the plasma formation rate above a threshold that depends on the material and laser parameters increases extremely strongly, in this parameter range the plasma formation process is also called "optical breakdown".

A high degree of precision during machining material by non-linear absorption requires that spatially localised reproducible small amounts of energy can be introduced into the material (deposited). Good spatial localisation is above all achieved by focusing the laser pulses by means of aberration-free optics having a high numerical aperture.

In the prior art it is assumed that a much better way to introduce little energy in conjunction with a high degree of reproducibility can be by ultra-short laser pulses having a duration in the range of a few femtoseconds up to a few picoseconds rather than with longer pulses (nanoseconds or even microseconds). For this there are above all three reasons:

1. The threshold that can be detected experimentally for the optical breakdown is usually equated with the observation of plasma luminescence—above all in the case of pulse durations in the nanosecond range.
2. The energy threshold for the formation of luminescent plasmas decreases strongly with a decrease in the pulse duration—approximately by a factor of 200 when the pulse duration is reduced from 10 ns to 100 fs. For nanosecond pulses, occurrence of a luminescent plasma is therefore linked to a much higher energy density and therefore associated with much stronger mechanical laser effects and side effects of the actual ablation of material.
3. Close to the threshold for the optical breakdown the laser effects generated by the conventional nanosecond pulses have a much wider scattering range than the femtosecond effects.

This has led to the view that the optical breakdown with nanosecond pulses be of a generally "statistic nature" while the femtosecond breakdown be "deterministic" and therefore better suited for reproducible machining of materials. The statement is furthermore justified that the occurrence of plasma luminescence during laser treatment with nanosecond pulses in principle conflicts with a precise localisation of the laser effects.

Regrettably, pulsed laser systems with pulse durations of less than 100 ps are complex systems with correspondingly high acquisition costs. Over and again compromises were sought that link the desire substantiated above for short-time pulses .with affordable equipment.

This is for example the case in the work by Colombelli et al., "Ultraviolet diffraction limited nanosurgery of live biological tissues", Rev. Sci. Instrum., Vol. 75, 472-478 (2004), where a UV chip laser (triple-frequency Nd:YAG) with a pulse duration of 500 ps is successfully used as a laser scalpel among others for individual cells. Such microchip lasers are relatively low priced, but typically also work with nanosecond pulses and in principle cannot fall below pulse durations of a few 100 ps.

According to the teachings of DE 198 55 623 C1 precise machining of materials with nanosecond pulses in transparent media is possible for carrying out the known inside laser engraving of glass; here even pulse durations of 100 ns are used. The patent specification however expressly states that wavelengths outside the plateau region of the transmittancy should be used, that are those for which the material precisely does not have an optimum degree of transparency. The importance of the occurrence of linear absorption that is necessitated thereby is emphasised by the authors but not explained in more detail.

A method for detecting very small transient changes in material are suggested in another patent application of the applicant (DE 10 2007 003 600.2). It's about a method for laser perforation of cell membranes that is as gentle as possible, where the pulsed laser light generates bubbles in the immediate vicinity of the cells in the focus. The size determination of the bubbles can take place via measuring the oscillation time by detecting the behaviour over time of the change in light intensity of a probe laser beam (cw laser, preferably another wavelength) that is guided together with the pulsed radiation (fs to ps pulses) through the laser focus during machining. Bubble sizes of as low as 150 nm have been detected in this way.

SUMMARY OF THE INVENTION

It is now the object of the invention to disclose a method for machining transparent media by means of a non-linear absorption that leads to precise localised changes of the material even when pulsed lasers with pulse durations in the nanosecond range are used.

The starting point of the invention is the discovery that when applying nanosecond pulses to a transparent material there is a radiation intensity range in which there is already a change in material without plasma luminescence occurring. This is below the known threshold value of the optical breakdown with which a far-reaching destruction is associated even outside the laser focus in the case of pulse durations in the nanosecond range.

The radiation intensity range that has been detected and is now to be utilised according to the invention is limited on both sides by measurable threshold values depending on the material (for example glass or water). The energy levels are clearly a function of the pulse duration and laser wavelength used, however the lower intensity level for the area of laser machining only varies rather weakly with the length of the pulses and the wavelength.

The higher threshold value is in each case indicated by the onset of plasma luminescence (in the following plasma luminescence threshold). After the onset of plasma luminescence an avalanche ionisation and thermal ionisation occur to such an extent that damage to the material is no longer limited to the laser focus.

In contrast, the lower threshold value is that one at which first material effects can be detected, in particular that material shows a local phase transition. An example for this is the start of the formation of bubbles in liquids (or cavities in solid bodies).

For clarification purposes let it already be mentioned at this point that all material changes are linked with the formation of a plasma in the present description. However, a discrimination has to be made between the luminescent plasma (see below high-density plasma) and that one which already occurs below the plasma luminescence threshold—but precisely above the low threshold value—and acts on the material but does not generate any far-reaching effects (see below low-density plasma).

The work of the applicant quoted in the prior art makes it possible to detect the low threshold value (in the following machining threshold) concretely, for example in water. This shows the general rule that the distance between the machining and plasma luminescence thresholds is the bigger, the shorter the wavelength used is selected and the longer the laser pulse duration is.

However, both threshold values evidently always coincide for pulse durations below 300 ps.

As has been stated at the start, the view prevails that precise laser machining of transparent materials can only be carried out effectively with ultra-short pulse lasers (pulse duration <100 ps). Therefore it is not surprising that the existence of precisely these separate threshold values with the intermediate radiation intensity range that can be used according to the invention for precise material machining so far remained hidden.

In order to formulate a directive for technical actions, the prejudice still has to be dispelled that in principle nanosecond pulse lasers would lead to statistically scattering laser effects.

BRIEF DESCRIPTION OF THE DRAWINGS

This shall take place in the following detailed explanation of the invention using the figures.

FIG. 1A shows the pulse shapes of the frequency-doubled ($\lambda$=532 nm) and FIG. 1B the pulse shapes of the frequency-tripled ($\lambda$=355 nm) laser radiation.

DETAILED DESCRIPTION OF THE INVENTION

Laser pulses originating from "normal" ns laser oscillators have distinctive intensity peaks due to the superposition of many longitudinal modes ("longitudinal mode beating") whose structure and amplitude change from pulse to pulse. In principle this fact has been known for a long time but the extent of the intensity overshoots relative to the pulse shape averaged over time or over many pulses does not reveal itself until after measurements with photo detectors and oscilloscopes with a high temporal resolution.

Figure 1:
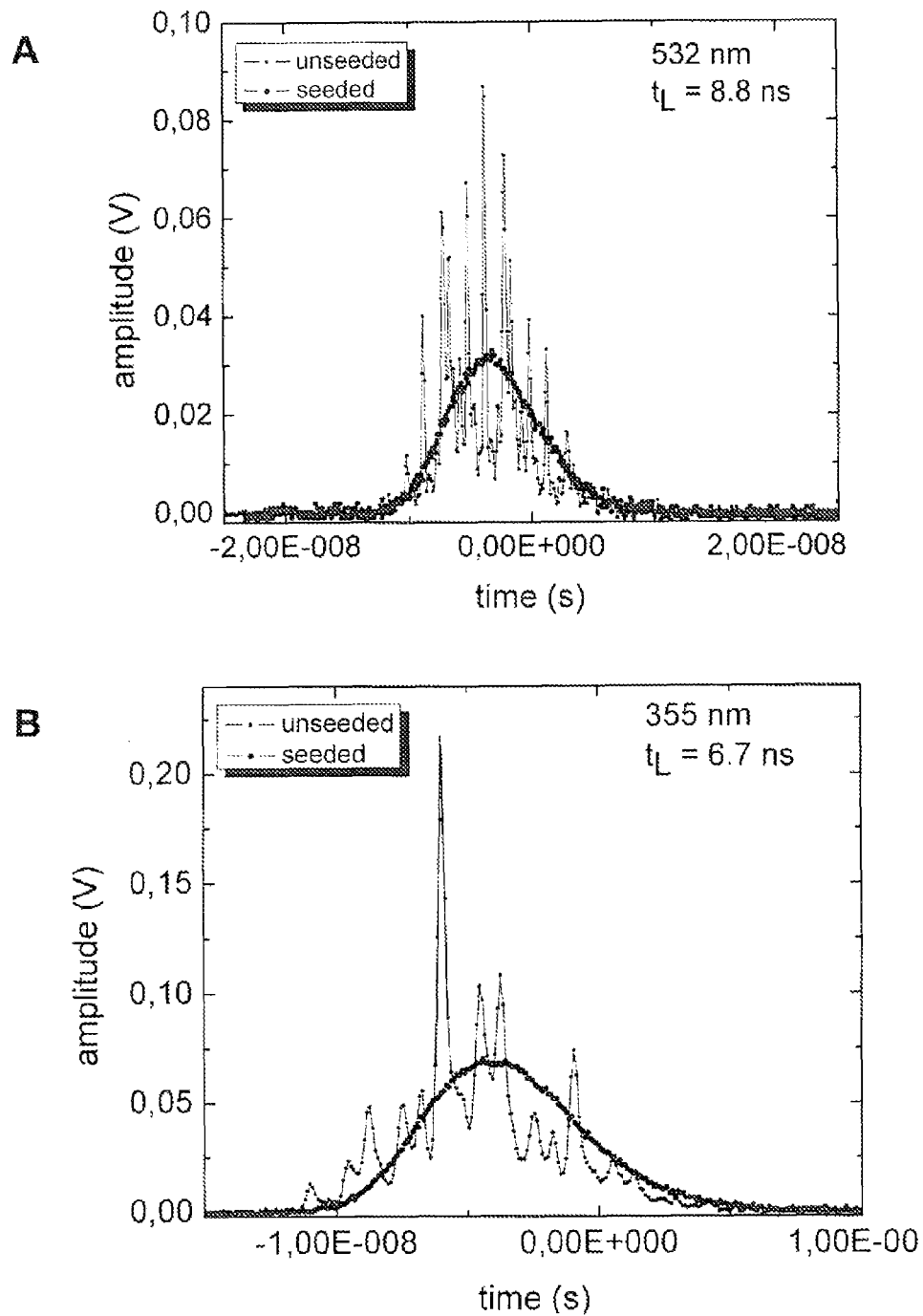
FIG. 1 shows the time course of the laser intensity for pulses of equal energy from a seeded and an unseeded (regular) Nd:YAG laser.

The measurement curves in FIG. 1 were recorded using a photo detector with a rise time <100 ps and an oscilloscope with 3 GHz bandwidth. From the measurement curves it is evident that the supposedly "statistic character" of the optical breakdown with nanosecond pulses is largely due to statistical variations of the laser pulses that have been used. With pulses that are temporally "smooth", for example Gaussian, a behaviour can be achieved that is considerably better to reproduce.

Gaussian laser pulses are emitted if only one longitudinal mode can start to oscillate in the laser resonator. This can be achieved by operating close to the laser threshold in combination with a short laser resonator and/or with an etalon in the resonator (the last two measures lead to a large frequency spacing of the longitudinal modes). As a rule, microchip lasers have a largely smooth pulse shape due to their short resonator length, but their maximum energy is limited to energies in the micro-joule range. In case there is an interest in Gaussian pulses with greater output energies, then a single-longitudinal-mode laser oscillator is used as a "seeder" for another oscillator with high output power in which the oscillation build-up of other longitudinal modes is suppressed by the strong amplification of the seed mode. For this purpose however, the resonator length L of the amplification oscillator has to be matched to the wavelength of the seeder so as to meet the resonator cycle condition L=n $\lambda$/2 which considerably increases the complexity of the entire system.

Figure 2:
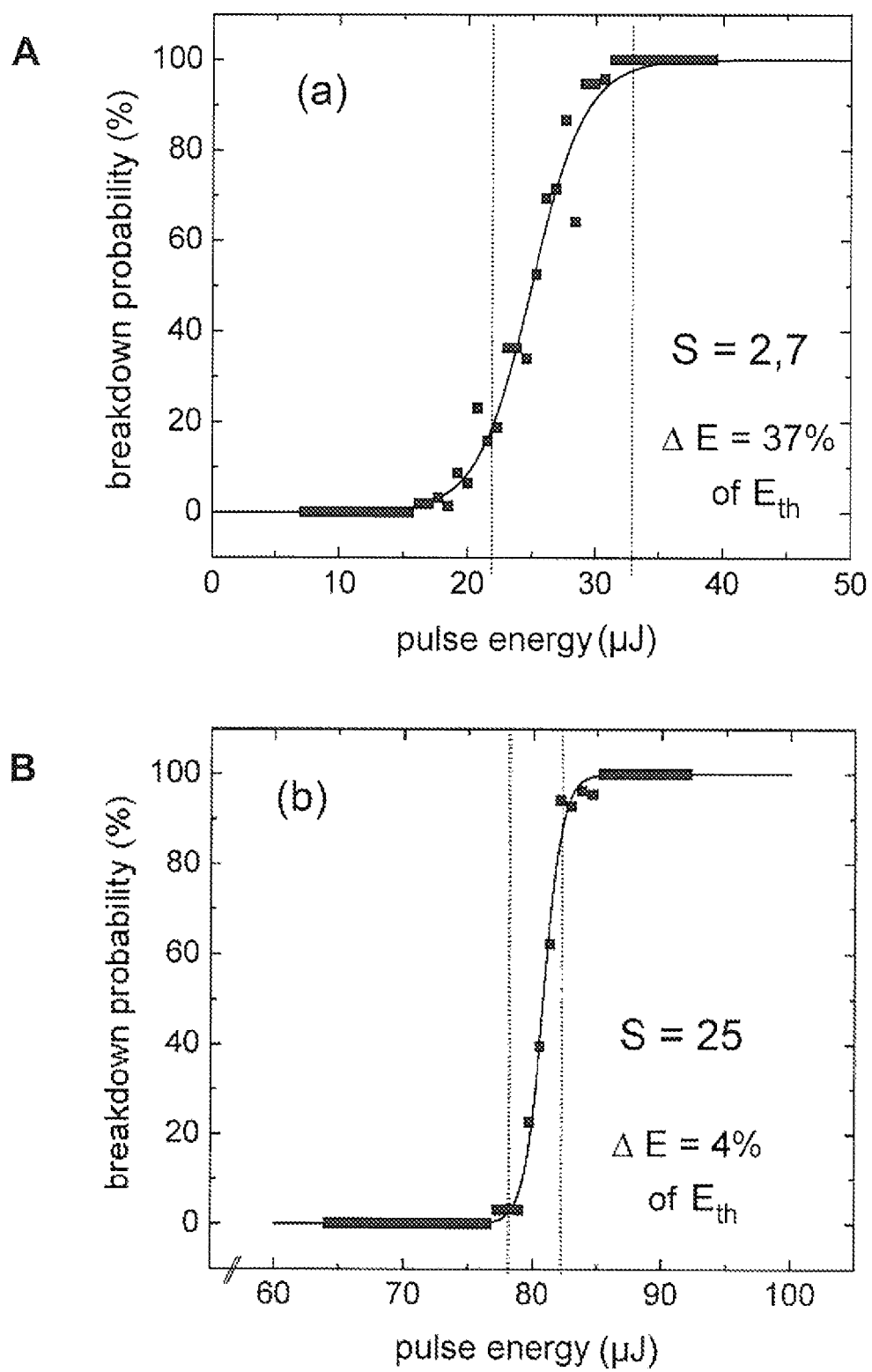
FIG. 2 shows the dependency of the breakdown probability of the laser pulse energy for the optical breakdown in water with (A) unseeded and (B) seeded laser pulses (focusing with NA=0.8, $\lambda$=1064 nm), the threshold for the optical breakdown being defined by the energy value $E_{th}$, where the breakdown probability amounts to 50%, and the threshold sharpness S corresponding to the ratio of $E_{th}$ to the energy interval dE in which the breakdown probability increases from 10% to 90%. A high value of S corresponds to a sharp, highly reproducible threshold. The drawing shows the measurement data for the machining threshold.

In actual fact, Gaussian pulses from a longitudinal single-mode laser resonator provide a considerably sharper threshold for the optical breakdown than regular pulses as is evident from the comparison in FIG. 2. The threshold sharpness S=$E_{th}$/$\Delta$E, with $\Delta$E=energy range between 10% and 90% breakdown likelihood, has the following values: S=2.7 for regular Nd:YAG nanosecond pulses ($t_L$=11.2 ns, $\lambda$=1064 nm, NA=0.8), S=25 for Gaussian nanosecond pulses ($t_L$=11.2 ns, $\lambda$=1064 nm, NA=0.8), and S=31 for femtosecond pulses ($t_L$=315 fs, $\lambda$=1040 nm, NA=0.8). Nanosecond pulses with a temporally smooth beam profile therefore generate an optical breakdown in a similarly reproducible and predictable manner like femtosecond pulses.

This deterministic character of the optical breakdown with nanosecond pulses can be adversely affected by impurities in the target material that can lead to the generation of starting electrons for the avalanche ionisation through linear absorption and thermal ionisation. If however large numerical apertures are used, the impurity density has to be very high to have such an effect. For example, the focus volume would thus contain an impurity only with a likelihood of 1% in the case of NA=0.8 (NA—numerical aperture) and an impurity density of $10^{10}$ cm$^{-3}$. Such a strong contamination only rarely occurs in practice and therefore a deterministic correlation between pulse energy and breakdown threshold can be assumed for a large class of cases when using temporally smooth ns laser pulses.

According to the invention it is therefore provided to use laser pulses with a smooth temporal beam profile for material machining. Generating nano and micro effects implies the use of temporally smooth laser pulses, but not their generation in a seeded laser system. Microchip lasers with a very short resonator likewise emit temporally smooth pulses that are suitable for generating the nano effects.

Figure 3:
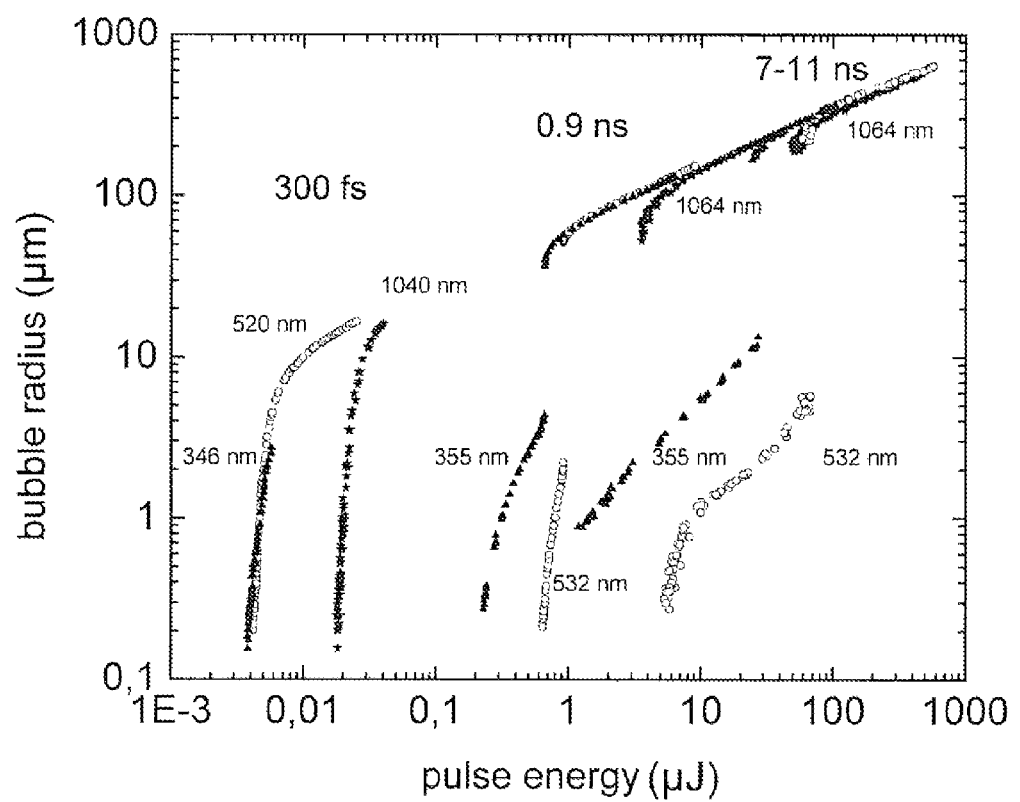
FIG. 3 shows the bubble radius as a function of the laser pulse energy for laser pulses of different duration and temporally smooth pulse shape (NA=0.8). The laser systems used for the measurement were a Yb:glass laser system with oscillator and regenerative amplifier for the 300 fs pulses, a Nd:YAG microchip laser for the 0.9 ns laser pulses and a seeded Nd:YAG laser for the pulses having a duration of 7-11 ns.

When investigating the optical breakdown in water with laser pulses from the UV, VIS and IR spectrum (Nd:YAG 1064 nm and $2^{nd}$ and $3^{rd}$ harmonics) the measurement values shown in FIG. 3 resulted. The measured bubble sizes are plotted versus the pulse energy irradiated in the focus. What has to be stressed in particular are the measurement values in the lower right image part (E<0.1 µJ, bubble radius <10 µm). They mark the start of the oscillation of bubbles that can be measured—and that are effective for example for treating cells—without any plasma luminescence occurring and whose size increases with the pulse energy.

Smooth nanosecond pulses as well as femtosecond pulses can be used to produce bubbles having a maximum radius of less than 1 µm. The energy interval available for producing bubble sizes <5 µm becomes wider and wider with an increase in the laser pulse duration. When the laser pulse energy is increased, the threshold for the formation of luminescent plasmas is eventually exceeded, which defines the upper limit of the inventive operating range.

Plasma luminescence starts at a sharply measurable plasma luminescence threshold. The occurrence of plasma luminescence is accompanied by an abrupt increase in the size of the plasma, the size of the bubbles produced, and the degree of conversion of laser energy into the mechanical energy of the bubbles. In FIG. 3, this transition is in each case marked by jumps in the value of the bubble radius. The spatial localizability and precision of the laser effects therefore drops drastically above the threshold for plasma luminescence.

Using femtosecond pulses, nano and micro effects can likewise be produced; there is, however, no separate area of small bubbles with a relatively slow rise in the bubble radius as it is observed using pulse durations of 0.9 to 11 ns. A separate area of small bubbles starts to form with pulse durations from approximately 300 ps, and its width (in the range of the laser pulse energies) increases with the pulse duration.

In the example that is discussed here, the machining threshold that is to be detected according to the present invention is the threshold for bubble formation, marked in FIG. 3 by the respective left end point of a row of measurement points.

It corresponds to the threshold for the phase transition in water and thus the threshold for material ablation by single pulses in water-containing materials such as for example biological tissue or cells. Even above the bubble formation threshold the bubbles initially stay very small, that is to say the laser effect has a very high spatial precision.

The machining threshold for water—expressed as irradiance—is between 90 GW/cm$^2$ and 170 GW/cm$^2$ for the wavelengths used of 355 nm and 532 nm and pulse durations 0.9 to 11 ns. The plasma luminescence thresholds for bright plasma luminescence and large bubbles are higher by a factor of 1.5 (at 1 ns, 532 nm) and 25 (at 1 ns, 355 nm) according to the pulse duration and the wavelength.

The energy range in which nano and micro effects can be produced with pulses with a pulse duration of between 0.9 and 11 ns is large and has sharp boundaries, and the effect sizes can be reproduced very well. It is therefore possible to produce nano and micro effects reliably and without statistic outliers.

For practical applications, a definite working point should be preferably defined, for example by means of that irradiance that first produces a predefined bubble size that is effective for the machining purpose. The working point should be at a certain distance from the plasma luminescence threshold so that the onset of plasma luminescence is avoided reliably. Up to now it was not known that such a working point can be found reliably at all.

In practice the irradiance is not only determined by the laser parameters but is also influenced by the light transmission path up to target point and the focusing conditions. It is therefore recommended to establish the machining threshold and the plasma luminescence threshold for the specific machining task before the method is employed, and possibly to record additional characteristics for the relation between pulse energy and effect strength.

Suitable in the case of solids are a microscopic inspection of the focus area or static light scattering methods (in transmission, at 90° or in reflection), in the case of liquids or tissue dynamic light scattering methods have to be used. In the state of the art, a possible realisation of this is referred to as bubble size measurement.

Light scattering methods are also suited for on-line inspection of nano and micromachining and as safety system during clinical and cosmetic tissue treatment where the occurrence of luminescent plasmas should immediately lead to an interruption of the treatment. The possibility of producing nano and micro effects without plasma luminescence was verified for numerical apertures in the range 0.25<NA<0.9, but is likely to be possible even with still larger or smaller apertures.

Wavelengths in the range of 300 nm to 1000 nm should be used. The laser light must be able to penetrate the target material. In the case of biological tissue and glass this requires wavelengths above 300 nm. At 1064 nm, no area with nano and micro bubbles is determined any longer. This results in the range mentioned.

The theoretical background of the occurrence of separated threshold values and in particular the limitation to wavelengths below approximately 1000 nm that was found can be simulated with the aid of model calculations. Their results are to be summarised briefly below:

The two-step nature of the optical breakdown process can be explained by modelling the formation of plasma while taking into account multi-photon ionisation, avalanche ionisation, diffusion losses, recombination, and thermal ionisation. Such a modelling is carried out for the first time within the framework of the investigation described here; earlier models as a rule took into account multi-photon ionisation, avalanche ionisation, and diffusion losses; recombination is usually mentioned, but neglected in the calculations, and thermal ionisation has so far not been taken into account at all when modelling the optical breakdown in transparent media.

The calculations show that the degree of ionisation at first rises fast with a rising laser intensity, but then almost stagnates on a plateau. In this range, the ionisation avalanche (proportional to the density $\rho$ of the free electrons and to the laser intensity) is slowed down by the recombination (proportional to $\rho^2$), so that a low-density plasma exists. Through multi-photon and avalanche ionisation, new free electrons are constantly produced during the laser pulse and they release their energy during recombination and heat up the medium. As soon as the spatial energy density deposited up to the end of the laser pulse exceeds the energy density required for a phase transition, a bubble (in water) or a cavity (in solids) is produced.

If the laser intensity increases still further, energy density and temperature increase in the laser focus until eventually thermal ionisation can occur to an appreciable extent. When thermal ionisation becomes so strong that, together with the avalanche ionisation, it overcomes the slowing-down action by recombination effects the degree of ionisation rises very rapidly until full ionisation is eventually reached. This increase at the upper end of the low-density plasma range leads to the production of a high-density plasma and corresponds to the occurrence of the intensive plasma luminescence that is usually identified with the optical breakdown by nanosecond pulses.

A transient equilibrium between avalanche ionisation and recombination processes during the laser pulse requires that the laser pulse duration is markedly longer than the time constant of the recombination. It can be assumed that a good upper estimate for this time constant for most transparent materials is approximately 100 ps. Consequently, the equilibrium cannot occur until at a pulse duration of a few hundred picoseconds. The experimental findings suggest a lower limit of 300 ps.

In the case of shorter pulse durations there is a smooth transition between the occurrence of bubble formation and the production of plasma luminescence at greater laser intensities or pulse energies. For longer pulse durations there is a separate low-density plasma range with a lower spatial energy density and particularly small bubbles and thereafter an abrupt rise in the degree of ionisation, the energy density, and the bubble size.

As a rule, start electrons for the ionisation avalanche have to be formed in transparent media by multi-photon ionisation for initiating the optical breakdown. At $\lambda=1064$ nm, this is the decisive hurdle for plasma formation, since a high-order multi-photon process is required because of the low photon energy. For example for overcoming the bandgap in water, the energy of six simultaneously absorbed photons is required. Therefore a very high intensity is required for producing the starting electrons. This intensity drives the following ionisation avalanche to very high densities of free electrons whose further rise can be stopped only for fractions of the laser pulse duration by recombination processes. Thereafter the temperature in the focus volume has risen to such high values that thermal ionisation and avalanche ionisation jointly drive the breakdown process further up to full ionisation. At $\lambda=1064$ nm, the optical breakdown leads to very high energy density levels, even at the bubble-formation threshold, far above the value required for a phase transition, and there exists no separate energy range in which micro effects can be produced.

This analysis can be applied to all transparent media with an energy band structure. From this it follows however that the inventive method is of a universally valid character and the possibility for producing nano and micro effects is not limited to water or aqueous media.

For UV/VIS nanosecond pulses, the calculations show a gradual rise of the degree of ionisation with the laser intensity in particular in the area of the phase transition (that is to say for example bubble formation). This means that there is a large number of free electrons even below the threshold for a phase transition and that the electron density can be adjusted by varying the laser intensity. It is therefore also possible using nanosecond pulses, to produce chemical or thermal effects without simultaneous phase transition that have been promoted by means of free electrons, as was described by Vogel et al. in Appl. Phys. B 81:1015-1047 (2005) for femtosecond pulses. According to the invention, a treatment threshold below the phase transition has to be defined for this goal that is now characterised by the onset of measurable changes in material, for example a change in the refractive index or structure transformations as a result of the presence of free electrons. This can for example be employed for writing waveguides with UV/VIS nanosecond pulses.

So as to differentiate from the patent specification DE 198 55 623 C1, it shall be stressed at this point that using the inventive method energy deposition is possible even in fully transparent media without linear absorption when using nanosecond pulses. The pulse duration of 100 ns that is used there is in all likelihood additionally not suited for the method described here, since such long pulses surely have no smooth temporal beam profile. Even single energy peaks during the course of the pulse can trigger plasma luminescence and would therefore destroy the localisation of the machining effect. Pulse lengths of up to a maximum of 20 ns should be preferably used.

A laser is also further provided that is suited in particular for the laser treatment of eye diseases. The inventive laser, for example a solid-state laser or a microchip laser, is designed for treating a transparent material, for example the cornea of the eye, by the non-linear absorption of pulsed laser radiation that takes place in the area of the laser focus, and has a wavelength in a range from 300 to 1000 nm, a pulse length in a range from 300 ps to 20 ns, and a means for setting the irradiance, the laser producing laser pulses with a temporally smooth beam profile.

According to the invention, the treatment success of the laser is verified by inspection means that register the treatment success and act on the means for setting the irradiance in such a way that the irradiance is within an interval between the detection limit of the inspection and the occurrence of plasma luminescence in the material treated.

The inspection means can preferably register, during the treatment, bubble formation taking place in the material treated, so that the detection limit of the inspection is defined by registering a first bubble formation. The upper limit of the interval is formed by the occurrence of plasma luminescence; this state, however, will not set in since the means for setting the irradiance are operative to the effect that the irradiance is within these interval limits. Irreparable damage to the eye can thus be prevented.

Finally the advantages of the invention shall be emphasised:

The spatial localizability is better than with ultra-short laser pulse durations because non-linear propagation effects can be neglected. At the treatment threshold the peak power in an UV nanosecond pulse is lower by two orders of magnitude than in the case of an UV femtosecond pulse.

Localised material treatment at target sites deep inside transparent materials can be carried out in a much simpler fashion using the inventive method than using femtosecond pulses because for this optics with a long working distance and therefore a usually relatively small numerical aperture are used as a rule. In this case, non-linear propagation effects and filamentation occur more easily when femtosecond pulses are used than when using the inventive method.

The usable energy range is larger than in the case of ultrashort laser pulse durations (see FIG. 3). Nanosecond lasers (above all microchip lasers) are much more cost-effective and compact than ultra-short pulse lasers.

The invention claimed is:

1. Method for treating a transparent material by non-linear absorption of pulsed laser radiation taking place in the area of a laser focus, having the following steps Selecting a laser wavelength from an interval from 300 ps to 1000 nm, Selecting a pulse length from an interval from 300 ps to 20 ns, Applying laser pulses with a temporal smooth beam profile, characterised in that an irradiance is selected from an interval predetermined for the material to be treated, in which plasma formation occurs without plasma luminescence.

2. Method according to claim 1, characterised in that the interval predetermined for the irradiance is determined as a function of the material to be treated by varying the irradiance in the laser focus by inspection of the treatment success, a lower interval limit of the irradiance being determined using a detection limit of the inspection and an upper interval limit using the occurrence of plasma luminescence.

3. Method according to claim 1, characterised in that the transparent material is a liquid medium and bubbles with a fixedly selected radius are formed in the liquid medium.

4. Method according to claim 3, characterised in that the transparent material is an aqueous medium and the irradiance for the aqueous medium is at least 90 $GW/cm^2$.

5. Method according of claim 1, characterised in that the transparent material is a solid and cavities are formed in the solid.

6. Method according to one of claim 1, characterised in that the transparent material is a solid and a refractive index in the solid is changed locally.

7. Method according to claim 1, characterised in that a pulse duration is at least three times a time constant of a plasma recombination of the material to be treated.

8. Method according to claim 1, characterised in that a pulse duration is selected from an interval from 0.9 to 11 ns.

9. Apparatus comprising:

a laser for treating a transparent material by non-linear absorption of pulsed laser radiation taking place in an area of a laser focus, having a wavelength in a range from 300 to 1000 nm and a pulse length in a range from 300 ps to 20 ns, means for setting an irradiance, the laser producing laser pulses with a temporally smooth beam profile, and inspection means that register a treatment success of the laser and act on the means for setting the irradiance in such a way that the irradiance is within an interval between a detection limit of the inspection and an occurrence of plasma luminescence in the material treated.

10. Apparatus according to claim 9, characterised in that the inspection means register bubble formation taking place during the treatment in the material treated.

11. Apparatus according to claim 9, characterised in that the laser is a seeded solid-state laser or a microchip laser.

\* \* \* \* \*